United States Patent [19]

Patchett

[11] 4,360,533
[45] Nov. 23, 1982

[54] GLYCERYL ESTER OF 1-METHYL-2-(3,4-DIHYDROXYPHENYL-)ALANINE

[75] Inventor: Arthur A. Patchett, Westfield, N.J.

[73] Assignee: Merck & Co., Inc., Rahway, N.J.

[21] Appl. No.: 330,543

[22] Filed: Dec. 14, 1981

[51] Int. Cl.³ .................... C07C 101/77; A61K 31/25
[52] U.S. Cl. ........................................ 424/309; 560/40
[58] Field of Search .................... 560/37, 40; 424/309

[56] References Cited

U.S. PATENT DOCUMENTS

| | | | |
|---|---|---|---|
| 2,868,818 | 1/1959 | Pfister et al. | 260/519 |
| 3,859,331 | 1/1975 | Kaiser et al. | 560/40 |
| 3,983,138 | 9/1976 | Saari | 260/326.43 |
| 4,221,813 | 2/1980 | Breault et al. | 424/309 |
| 4,254,273 | 3/1981 | Powell et al. | 560/40 |

*Primary Examiner*—James H. Reamer
*Attorney, Agent, or Firm*—Martin L. Katz; Daniel T. Szura

[57] ABSTRACT

Glyceryl esters of 1-methyl-2-(3,4-dihydroxyphenyl-)alanine, pharmaceutical compositions and method of treatment are disclosed.

6 Claims, No Drawings

GLYCERYL ESTER OF 1-METHYL-2-(3,4-DIHYDROXYPHENYL)ALANINE

BACKGROUND OF THE INVENTION

The present invention concerns a glyceryl ester of 1-methyl-2-(3,4-dihydroxyphenyl)alanine and its use as an antihypertensive agent.

L-1-Methyl-2-(3,4-dihydroxyphenyl)alanine is a commercial antihypertensive agent. It is also referred to as L-α-methyldopa. Esters of L-α-methyldopa are also known (see e.g. U.S. Pat. Nos. 2,868,818; 3,983,138; and 4,221,813).

A glyceryl ester of α-methyldopa has been discovered. It is an active antihypertensive agent.

SUMMARY OF THE INVENTION

Glyceryl ester of α-methyldopa of the formula

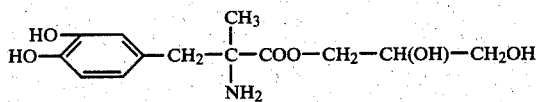

and its use as antihypertensive agents.

DETAILED DESCRIPTION OF THE INVENTION

An embodiment of this invention is a compound of the formula

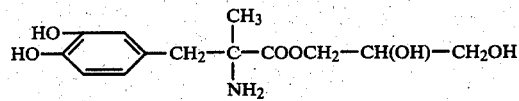

and pharmaceutically acceptable salts thereof.

Pharmaceutically acceptable salts of I include salts with inorganic acids such as the hydrohalides, especially HCl, a phosphoric acid, nitric acid, sulfuric acid as well as organic acids including carboxylic acids such as acetic acid, maleic acid, malic acid, heptanoic acid, pamoic acid, oxalic acid, pivalic acid, succinic acid and the like, and non-carboxylic acids such as isethionic acid, methanesulfonic acid and the like. The hydrohalide salts are preferred inorganic acid salts. Preferred organic acid salts are the maleate, the pivaloate the succinate, the oxalate, the pamoate and the isethionate. The salts of I are prepared using conventional procedures e.g., by treating the free base I with a suitable acid in a liquid reaction medium.

The formula I compound has two chiral centers, one at $-C(CH_3)(NH_2)$-position and one at the $-CHOH$-position. These chiral centers confer optical activity in the compound. The symbols L and D, l and d, + and −, S and R or combinations of these symbols are used to designate the stereochemical configuration at these chiral centers. Since there are two optical centers in I, there are four possible diastereomers which may be designated e.g., as S,S; S,R; R,S; R,R or L,L; L,D; D,L; D,D. Where no isomer designation is indicated when identifying a compound, all configurations, that is, the individual enantiomers, racemates and mixtures of diastereomers and enantiomers are included.

A preferred formula I compound is one where the configuration at $-C(CH_3)(NH_2)-$ is the L-form, substantially free of the D-form.

The compounds of formula I and their salts are useful for treating hypertension in hypertensive mammals, including humans. Administration of the I compound may be oral or parenteral in any suitable dosage form. Suitable oral dosage forms are tablets, capsules, elixirs, suspensions, emulsions and the like. Parenteral dosage forms may be solutions, suspensions, emulsions and the like. The compound may also be administered in an appropriate continuous release formulation—or via a controlled metering device implanted in or ingested by the hypertensive patient.

The suitable dosage forms are prepared using conventional procedures and utilizing conventional compounding ingredients, diluents, carriers and the like. The dosage forms will contain an amount of compound I sufficient to be useful in effecting the desired antihypertensive response in the patient.

The dosage of compound I may be varied. Useful daily dosage may range from about 100 mg to about 5000 mg, preferably from about 250 mg to about 3000 mg and more preferably from about 250 mg to about 1500 mg.

The present formula I compounds have good oral activity.

Any convenient process may be used for preparing the present ester.

The following examples and reaction equations are illustrative of a preferred process for the preparation of an ester of formula I. All temperatures are in degrees Celsius.

EXAMPLE 1

Preparation of α-Glyceryl ester of L-1-methyl(2-(3,4-dihydroxyphenyl)alanine.HCl

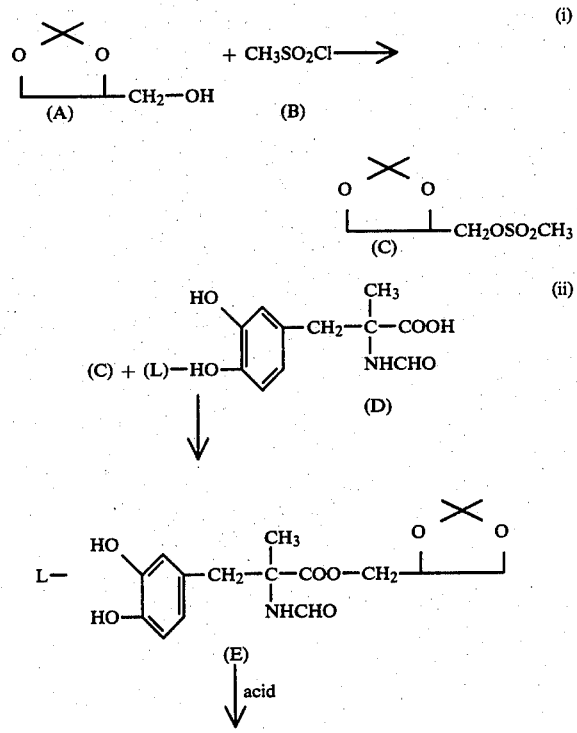

-continued

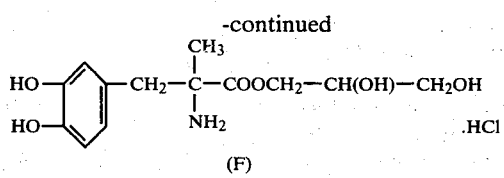

(F)

(A) Isopropylidene glyceryl-α-mesylate (C)

To a solution of 20 ml of isopropylidene glycerol (A) and 33.5 ml of triethylamine in 500 ml of CH$_2$Cl$_2$ was added 13.6 ml of methanesulfonyl chloride (B) keeping the temperature at about 0°. This reaction mixture was stirred at 0° for about 30 minutes. The reaction mixture was then washed with 300 ml of ice water, 200 ml of water containing 13.8 g of NaH$_2$PO$_4$, 200 ml of saturated NaHCO$_3$ solution and 200 ml of saturated NaCl solution. After drying over Na$_2$SO$_4$, the methylene chloride solution was evaporated, under vacuum, to dryness to yield 32 g of isopropylideneglyceryl-α-mesylate (C). The NMR spectrum showed methyl absorption at 1.37, 1.43 and 3.07.

(2) Isopropylidene glyceryl ester of N-formyl-L-α-methyldopa (E)

A mixture of 5.0 g of N-formyl-L-α-methyldopa (D), 10.0 g of isopropylidene glyceryl α-mesylate, 5.0 g of NaHCO$_3$ and 5.0 g of NaI in 100 ml of dimethylformamide (DMF) was stirred under nitrogen at 100° for 9 hours. After cooling, the reaction mixture was diluted with 200 ml of water and extracted with 4×100 ml of ethyl acetate. The combined ethyl acetate extracts were washed with 100 ml of water, dried over Na$_2$SO$_4$ and evaporated to dryness to give 11.7 g of a liquid crude product. This crude product was purified by column chromatography first over Sephadex and then over silica gel to yield 2.1 g of a gum which gave a single spot by thin layer. spectrogram showed peaks at 353 (+), 348 (+—CH$_3$) 309, 296, 250, 231, 216 and 194.

(3) α-Glyceryl ester of L-α-Methyldopa (F)

A solution of 1.8 g of the isopropylidene glyceryl ester of N-formyl-L-α-methyldopa (E) and 1.8 ml of hydrochloric acid in 18 ml of isopropyl alcohol was heated at 53° for six hours. After evaporating to dryness under vacuum and flashing with toluene, 1.5 g of an amorphous solid was obtained. This solid was dissolved in 20 ml of water, treated with decolorizing carbon, filtered and isolated by freeze drying to give a glassy solid (F). The NMR spectrum showed no isopropylidene or formyl functionality. The mass spectrum of silylated solid (F) had peaks at 630 (pentasilyl derivative-15) and 558 (tetrasilyl derivative-15).

Claims to the invention follow.

What is claimed is:

1. A compound of the formula

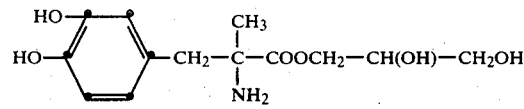

and pharmaceutically acceptable salts thereof.

2. The compound of claim 1 having the L-configuration at the —C(CH$_3$)(NH$_2$)— chiral center.
3. The hydrochloride salt of the claim 1 compound.
4. The hydrochloride salt of the claim 2 compound.
5. A pharmaceutical composition useful for treating hypertension containing a claim 1 compound.
6. A method of treating hypertension which comprises administering an effective dose of a compound of claim 1.

* * * * *